US007517908B2

(12) United States Patent
Krishnan et al.

(10) Patent No.: US 7,517,908 B2
(45) Date of Patent: *Apr. 14, 2009

(54) METHOD FOR AUGMENTING THE EFFECTS OF SEROTONIN REUPTAKE INHIBITORS

(75) Inventors: Ranga R. Krishnan, Chapel Hill, NC (US); Marc G. Caron, Hillsborough, NC (US); Xiaodong Zhang, Durham, NC (US); Martin Beaulieu, Durham, NC (US); Raul R. Gainetdinova, Chapel Hill, NC (US); Tatiana D. Sotnikova, Chapel Hill, NC (US)

(73) Assignee: Duke University, Durham, NC (US)

( * ) Notice: Subject to any disclaimer, the term of this patent is extended or adjusted under 35 U.S.C. 154(b) by 156 days.

This patent is subject to a terminal disclaimer.

(21) Appl. No.: 11/133,867

(22) Filed: May 20, 2005

(65) Prior Publication Data

US 2006/0142375 A1    Jun. 29, 2006

Related U.S. Application Data (60) Provisional application No. 60/642,869, filed on Jan. 11, 2005, provisional application No. 60/642,800, filed on Jan. 11, 2005, provisional application No. 60/629,951, filed on Nov. 22, 2004, provisional application No. 60/606,811, filed on Sep. 2, 2004, provisional application No. 60/573,265, filed on May 21, 2004.

(51) Int. Cl.
*A01N 43/08* (2006.01)
*A61K 31/34* (2006.01)
*G01N 33/566* (2006.01)
*G01N 33/567* (2006.01)
*C12Q 1/00* (2006.01)
*C12Q 1/68* (2006.01)

(52) U.S. Cl. .................. 514/469; 436/504; 436/503; 436/501; 435/6; 435/4

(58) Field of Classification Search .................. None
See application file for complete search history.

(56) References Cited

U.S. PATENT DOCUMENTS

| | | | |
|---|---|---|---|
| 4,920,122 A * | 4/1990 | Naruse et al. ............... 514/250 |
| 5,595,772 A | 1/1997 | Wurtman et al. | |
| 5,958,429 A | 9/1999 | Wong | |
| 6,011,054 A | 1/2000 | Oxenkrug et al. | |
| 6,013,622 A | 1/2000 | Bruno et al. | |
| 6,191,133 B1 | 2/2001 | Coppen | |
| 6,211,171 B1 | 4/2001 | Sawynok et al. | |
| 6,218,395 B1 | 4/2001 | Swartz | |
| 6,239,162 B1 | 5/2001 | Oxenkrug | |
| 6,358,944 B1 | 3/2002 | Lederman et al. | |
| 6,368,814 B1 | 4/2002 | Ghoshal et al. | |
| 6,369,051 B1 | 4/2002 | Jenkins | |
| 6,387,907 B1 | 5/2002 | Hendricks et al. | |
| 6,387,936 B1 | 5/2002 | Blanchard-Bregeon et al. | |
| 6,387,956 B1 | 5/2002 | Shapira et al. | |
| 6,472,423 B1 | 10/2002 | Ross et al. | |
| 6,492,366 B1 | 12/2002 | Lavielle et al. | |
| 6,500,829 B1 | 12/2002 | Wood et al. | |
| 6,552,014 B2 | 4/2003 | Serebruany et al. | |
| 6,579,899 B1 | 6/2003 | Wurtman et al. | |
| 6,656,172 B1 | 12/2003 | Hildebrand | |
| 6,673,381 B2 | 1/2004 | Bailey et al. | |
| 6,808,725 B2 | 10/2004 | Bailey et al. | |
| 2006/0029951 A1 | 2/2006 | Caron et al. | |

FOREIGN PATENT DOCUMENTS

WO    WO 2004/007704 A2    1/2004

OTHER PUBLICATIONS

Blakely, Neuron, 2005, vol. 48, pp. 701-702.*
Zhang et al., Neuron, 2005, vol. 48, pp. 705-706.*
Zhou et al., Neuron, 2005, vol. 48, pp. 702-703.*
Bogaert et al., Neuron, 2005, vol. 48, pp. 704.*
Glatt et al, Neuron, 2005, vol. 48, pp. 704-705.*
Erlandsen et al.; "Correction of kinetic and stability defects by tetrahydrobiopterin in phenylketonuria patients with certain phenylalanine hydroxylase mutations" *PNAS* 101:48 16903-16908 (2004).
Sánchez; "R-citalopram attenuates anxiolytic effects of escitalopram in a rat ultrasonic vocalisation model" *European Journal of Pharmacology* 464 155-158 (2003).
Van Pragg; "Serotonin precursors in the treatment of depression" *Adv Biochem Psychopharmacol.* 34 259-286 (1982). Abstract Only.
Zill et al.; "SNP and haplotype analysis of a novel tryptophan hydroxylase isoform (TPH2) gene provide evidence for association with major depression" *Molecular Psychiatry* 1-7 (2004).
Zill et al.; "Single Nucleotide Polymorphism and Haplotype Analysis of a Novel Tryptophan Hydroxylase Isoform (TPH2) Gene in Suicide Victims" *Biol Psychiatry* 56 581-586 (2004).
Aghajanian et al.; "Serotonin model of schizophrenia: emerging role of glutamate mechanisms" *Brain Res Brain Res Review* 31 302-312 (2000).
Blier et al.; "Putative mechanisms of action of antidepressant drugs in affective and anxiety disorders and pain" *J Psychiatry Neurosci* 26 37-43 (2001).
Fitzpatrick ; "Tetrahydropterin-dependent amino acid hydroxylases" *Annu Rev Biochem* 68 355-381 (1999).
Flattem et al.; "Modified structure of the human serotonin transporter promotor" *Mol Psychiatry* 5 110-115 (2000).
Frazer; "Pharmacology of antidepressants" *J Clin Psychopharmacol* 17:Suppl 1 2S-18S (1997).

(Continued)

*Primary Examiner*—Olga N. Chernyshev
(74) *Attorney, Agent, or Firm*—Myers Bigel Sibley & Sajovec, P.A.

(57) ABSTRACT

A method of treating a subject for a serotonergic neurotransmission dysregulation disorder, comprises administering the subject a serotonin enhancer (e.g., a serotonin reuptake inhibitor) in an amount effective to treat the disorder; and concurrently administering the subject 5-hydroxytryptophan in an amount effective to enhance the activity of the serotonin enahancer, (e.g., serotonin reuptake inhibitor). In preferred embodiments the disorder is depression, anxiety, or substance abuse.

5 Claims, 1 Drawing Sheet

OTHER PUBLICATIONS

Geyer; "Serotonergic functions in arousal and motor activity" *Behav Brain Res* 73 31-35 (1996).

Tamminga; "Serotonin and schizophrenia" *Biol Psychiatry* 44 1079-1080 (1998).

Tecott; "The genes and brains of mice and men" *Am J Psychiatry* 160 646-656 (2003).

Veenstra-VanderWeele et al.; "Pharmacogenetics and the serotonin system: initial studies and future directions" *Eur J Pharmacol* 410 165-181 (2000).

Walther et al.; "Synthesis of serotonin by a second tryptophan hydroxylase isoform" *Science* 299 76 (2003).

Walther et al.; "A unique central tryptophan hydroxylase isoform" *Biochem Pharmacol* 66 1673-1680 (2003).

Lucki; "The spectrum of behaviors influenced by serotonin" *Biol Psychiatry* 44 151-162 (1998).

Pey et al.; "Phenylketonuria: genotype-phenotype correlations based on expression analysis of structural and functional mutations in PAH" *Hum Mutat* 21:4 370-378 (2003).

Gainetdinov et al.; "Role of serotonin in the paradoxical calming effect of psychostimulants on hyperactivity" *Science* 283 397-401 (1999).

Bonasera et al.; "Mouse models of serotonin receptor function: toward a genetic dissection of serotonin systems" *Pharmacol Ther* 88 133-142 (2000).

Gingrich et al.; "Dissecting the role of the serotonin system in neurophychiatric disorders using knockout mice" *Psychopharmacology* 155 1-10 (2001).

Murphy et al.; "Experimental gene interaction studies with SERT mutant mice as models for human polygenic and epistatic traits and disorders" *Genes Brain Behav* 2 350-364 (2003).

Lucki et al.; "Sensitivity to the effects of pharmacologically selective antidepressants in different strains of mice" *Psychopharmacology (Beri)* 155 315-322 (2001).

Stenfors et al.; "Pharmacological characterisation of the decrease in 5-HT synthesis in the mouse brain evoked by the selective serotinin re-uptake inhibitor citalopram" *Naunyn Schmiedebergs Arch Pharmacol* 363 222-232 (2001).

Parker et al.; "Assessing the comparative effectiveness of antidepressant therapies: a prospective clinical practice study" *J Clin Psychiatry* 62 117-125 (2001). *Abstract only*.

Martin; "Serotonin syndrome" *Ann Emerg Med* 28 520-526 (1996).

Patel et al.; "Robust and tissue-specific expression of TPH2 versus TPH1 in rat raphe and pineal gland" *Biol Psychiatry* 55 428-433 (2004).

Broquet; "Status of treatment of depression" *South Med J* 92 846-856 (1999).

Garriock HA et al. Lack of association of TPH2 exon XI polymorphisms with major depression and treatment resistance. Molecular Psychiatry 10:976-977. Jul. 12, 2005.

Correspondence from Blakely; Zhou et al; Bogaert et al; Glatt et al. and Zhang et al. Neuron 48:701-706. Dec. 8, 2005.

Delorme R et al. No human tryptophan hydroxylase-2 gene R441H mutation in a large cohort of psychiatric patients and control subjects. Biological Psychiatry 60:202-203. 2006.

Sacco R et al. Case-control and family-based association studies of candidate genes in autistic disorder and its endophenotypes: TPH2 and GLO1. BMD Medical Genetics 8(11):1471-1480. Mar. 8, 2007.

Sheehan K et al. No association between TPH2 gene polymorphisms and ADHD in a UK sample. Neuroscience Letters 412(2):105-107. Jan. 29, 2007.

Peters EJ et al. Investigation of serotonin-related genes in antidepressant response. Molecular Psychiatry 9:879-889. Mar. 30, 2004.

Zhang X et al. Tryptophan hydroxylase-2 controls brain serotonin synthesis. Science 305:217. Jul. 9, 2004.

Zhang X et al. Functional polymorphisms of the brain serotonin synthesizing enzyme tryptophan hydroxylase-2. Cell. Mol. Life Sci. 63:6-11. 2006.

Winge I et al. Characterization of wild-type and mutant forms of human tryptophan hydroxylase 2. Journal of Neurochemistry 100:1648-1657. 2007.

Gainetdinov R R and Caron M G. Monoamine Transporters: From Genes to Behavior. Annu. Rev. Pharmacol. Toxicol. (2003), vol. 43, pp. 261-284.

Cervo L et al. Geno-type dependent activity of tryptophan hydroxylase-2 determines the response to citalopram in a mouse model of depression. The Journal of Neuroscience (Sep. 7, 2004), vol. 25, No. 36, pp. 8165-8172.

Beaulieu J-M et al. Role of GSK3β in behavioral abnormalities induced by serotonin deficiency. PNAS (Jan. 29, 2008), vol. 105, No. 4, pp. 1333-1338.

Fulmer T. The great (mouse) depression. Science-Business eXchange (Feb. 7, 2008), vol. 1, No. 2, pp. 1, 10-11.

International Search Report and Written Opinion, PCT/US05/17952, mailed Mar. 18, 2008.

Côte F et al. Disruption of the nonneuronal *tph1* gene demonstrates the importance of peripheral serotonin in cardiac function. PNAS USA (Nov. 13, 2003), vol. 100, No. 23, pp. 13525-13530.

De Luca et al. Analysis of the novel TPH2 gene in bipolar disorder and suicidality. Molecular Psychiatry (2004), vol. 9, pp. 896-897.

McKinney J et al. A loss-of-function mutation in tryptophan hydroxylase 2 segregating with attention-deficit/hyperactivity disorder. Molecular Psychiatry (2008), vol. 13, pp. 365-367.

Walther D J et al. Synthesis of serotonin by a second tryptophan hydroxylase isoform. Science (Jan. 3, 2003), vol. 299, p. 76, *Supporting Online Material*, pp. 1-7.

International Search Report and Written Opinion, PCT/US05/17856, mailed Jul. 9, 2008.

* cited by examiner

Figure 1

METHOD FOR AUGMENTING THE EFFECTS OF SEROTONIN REUPTAKE INHIBITORS

RELATED APPLICATIONS

This application claims the benefit of U.S. Provisional Patent Application Ser. No. 60/642,869 filed Jan. 11, 2005, and of U.S. Provisional Patent Application Ser. No. 60/642,800, filed Jan. 11, 2005, and of U.S. Provisional Patent Application Ser. No. 60/629,951, filed Nov. 22, 2004, and of U.S. Provisional Patent Application Ser. No. 60/606,811, filed Sep. 2, 2004, and of U.S. Provisional Patent Application Ser. No. 60/573,265, filed May 21, 2004, the disclosures of all of which are incorporated by reference herein in their entirety.

This application is related to Marc G. Caron, Xiaodong Zhang, Martin Beaulieu, Raul R. Gainetdinov, Tatiana D. Sotnikova, Ranga R. Krishnan, David A. Schwartz, Lauranell Burch, and Redford B. Williams, Polymorphism in Tryptophan Hydroxylase-2 Controls Brain Serotonin Synthesis, U.S. patent application Ser. No. 11/133,949, filed May 20, 2005, and published as US 20060029951, the disclosure of which is incorporated by reference herein in its entirety.

This invention was made with Government support under grant numbers 5 P50 MH60451 and 5 P50 MH60451 from the National Institute of Mental Health. The United States Government has certain rights to this invention.

FIELD OF THE INVENTION

The present invention relates to methods for the treatment of serotonin neurotransmission dysregulation disorders, including but not limited to depression, anxiety and substance abuse.

BACKGROUND OF THE INVENTION

Brain serotonin system plays a critical role in numerous neuronal functions and dysregulation of its homeostasis may contribute to many psychiatric disorders (Veenestra-Vander-Weele et al, 2000; Flattem and Blakely 2000; Blier and Abbott 2001; Tecott, 2003; Geyer, 1996; Tamminga, 1998; Snyder and Peroutka, 1982; Frazer, 1997; Aghajanian and Marek, 2000). In fact, numerous conditions such as unipolar major depression and bipolar disorder, obsessive-compulsive disorder, anxiety, autism, personality disorder, panic and eating disorders, suicidality, chronic pain and post-traumatic stress syndrome and even attention deficit hyperactivity disorder (ADHD), are effectively treated by raising the extracellular concentrations of serotonin in the brain with compounds including selective serotonin reuptake inhibitors (SSRIs) that inhibit the neuronal re-uptake of serotonin. Like many other neurotransmitters and modulators, the actions of serotonin are modulated by the delicate balance between synthesis and degradation of this monoamine. Tryptophan hydroxylase-1 (Tph1) has long been considered as the sole rate-limiting enzyme for the synthesis of serotonin. However, Walther et al (2003) recently reported that inactivation of the Tph1 gene in the mouse led to a decrease in the peripheral levels of serotonin but no changes in central serotonin levels, suggesting that another form of the enzyme might exist. Data base mining yielded a second related gene that was identified, cloned and named TPH2. The product of the TPH2 gene is preferentially expressed in the brain as opposed to the predominant peripheral expression pattern of TPH1 (Walther et al, 2003).

M. Bader et al., PCT Application WO 2004/007704 (US 2006/0275759), describes the identification of TPH2.

SUMMARY OF THE INVENTION

A first aspect of the present invention is a method of treating a subject for a serotonergic neurotransmission dysregulation disorder, comprising: administering the subject a serotonin enhancer (e.g., a serotonin reuptake inhibitor) in an amount effective to treat the disorder; and concurrently administering the subject 5-hydroxytryptophan in an amount effective to enhance the activity of the serotonin enahancer, (e.g., serotonin reuptake inhibitor). In preferred embodiments the disorder is depression, anxiety, or substance abuse.

A second aspect of the present invention is a method of treating a subject for a serotonergic neurotransmission dysregulation disorder, comprising: administering the subject a serotonin enhancer (e.g., a serotonin reuptake inhibitor) in an amount effective to treat the disorder; and concurrently administering the subject a peripheral decarboxylase inhibitor such as carbidopa in an amount effective to enhance the activity of the serotonin enhancer (e.g., selective serotonin reuptake inhibitor).

A third aspect of the invention is a method of treating a subject for a serotonergic neurotransmission dysregulation disorder, comprising: administering the subject a serotonin enhancer (e.g., a serotonin reuptake inhibitor) in an amount effective to treat said disorder; and concurrently administering the subject a BH4 enhancer such as tetrahydrobiopterin in an amount effective to enhance the activity of the serotonin enahancer (e.g., serotonin reuptake inhibitor).

A fourth aspect of the present invention is a method of treating a subject for a serotonergic neurotransmission dysregulation disorder, comprising: determining the presence or absence of at least one Tph2 mutation in the subject; and then, if the subject possesses at least one Tph2 mutation; administering the subject 5-hydroxytryptophan in an amount effective to treat the disorder.

A fifth aspect of the present invention is a method of treating a subject for a serotonergic neurotransmission dysregulation disorder, comprising: determining the presence or absence of at least one Tph2 mutation in the subject; and then, if the subject possesses at least one Tph2 mutation; administering the subject a peripheral decarboxylase inhibitor in an amount effective to treat the disorder.

A sixth aspect of the present invention is a method of treating a subject for a serotonergic neurotransmission dysregulation disorder, comprising: determining the presence or absence of at least one Tph2 mutation in said subject; and then, if said subject possesses at least one Tph2 mutation; administering said subject a BH4 enhancer such as tetrahydrobiopterin in an amount effective to treat said disorder.

In some embodiments of the foregoing, the disorder is depression, anxiety, or substance abuse; in other embodiments the disorder is another serotonergic neurotransmission dysregulation disorder such as described below.

A further aspect of the present invention is a pharmaceutical formulation comprising, consisting of, or consisting essentially of:

(a) a serotonin enhancer such as a serotonin reuptake inhibitor;

(b) a serotonin precursor such as 5-hydroxytryptophan;

(c) optionally, but in some embodiments preferably, a peripheral decarboxylase inhibitor such as carbidopa;

(d) optionally, but in some embodiments preferably, a BH4 enhancer such as tetrahydrobiopterin; and (e) a pharmaceutically acceptable carrier.

A further aspect of the present invention is a pharmaceutical formulation comprising, consisting of, or consisting essentially of:

(a) a serotonin enhancer such as a serotonin reuptake inhibitor;

(b) a peripheral decarboxylase inhibitor such as carbidopa;

(c) optionally, but in some embodiments preferably, a BH4 enhancer such as tetrahydrobiopterin;

(d) optionally, but in some embodiments preferably, a serotonin precursor such as 5-hydroxytryptophan; and (e) a pharmaceutically acceptable carrier.

A further aspect of the present invention is a pharmaceutical formulation comprising, consisting of, or consisting essentially of:

(a) a serotonin enhancer such as a serotonin reuptake inhibitor;

(b) a BH4 enhancer such as tetrahydrobiopterin;

(c) optionally, but in some embodiments preferably, a peripheral decarboxylase inhibitor such as carbidopa;

(d) optionally, but in some embodiments preferably, a serotonin precursor such as 5-hydroxytryptophan; and (e) a pharmaceutically acceptable carrier.

A further aspect of the present invention is a pharmaceutical formulation comprising, consisting of, or consisting essentially of:

(a) a serotonin precursor such as 5-hydroxytryptophan;

(b) a peripheral decarboxylase inhibitor such as carbidopa;

(c) optionally, but in some embodiments preferably, a BH4 enhancer such as tetrahydrobiopterin; and (d) a pharmaceutically acceptable carrier.

A further aspect of the present invention is a pharmaceutical or neutraceutical formulation comprising, consisting of, or consisting essentially of:

(a) a serotonin precursor such as 5-hydroxytryptophan; and (b) a BH4 enhancer such as tetrahydrobiopterin; and (c) a pharmaceutically acceptable carrier; or in the case of a neutraceutical optionally other food ingredients such as fats, proteins, and/or carbohydrates.

A further aspect of the present invention is the use of 5-hydroxytryptophan for the preparation of a medicament for carrying out a method of as described herein.

A further aspect of the present invention is the use of a peripheral decarboxylase inhibitor such as carbidopa for the preparation of a medicament for carrying out a method as described herein.

A further aspect of the present invention is the use of a BH4 enhancer such as tetrahydrobiopterin for the preparation of a medicament for carrying out a method as described herein.

A further aspect of the present invention is the use of a serotonin enhancer such as a serotonin reuptake inhibitor for the preparation of a medicament for carrying out a method as described herein.

A still further aspect of the present invention is the use of a means for detecting a Tph2 mutation for carrying out a method as described herein.

The foregoing and other objects and aspects of the present invention are explained in greater detail in the drawings herein and the specification set forth below.

DETAILED DESCRIPTION OF THE PREFERRED EMBODIMENTS

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The disclosures of all United States Patent references cited herein are to be incorporated by reference herein in their entirety.

1. Definitions.

"Genotyping" as used herein means determination of the type and number of alleles present in a subject, whether determined by nucleic acid sequencing, PCR or RT-PCR amplification, examination of Tph2 protein, or any other method. A specific gene can be genotyped to determine if the gene is a wild-type or variant allele. Genotyping does not require sequencing of the entire gene but may simply involve determining the presence or absence of one or more mutations therein, as compared to the "wild type" gene.

"Tph2 mutation" as used herein refers to any mutation which leads to loss or decrease in activity of the encoded protein (tryptophan hydroxylase-2), such that the conversion of tryptophan to 5-hydroxytryptophan in the subject by tryptophan hydroxylase-2 is reduced.

"Serotonin enhancer" as used herein refers to any compound that increases, directly or indirectly, the availability of serotonin in the central nervous system for binding to serotonin receptors at the post-synaptic membrane, including but not limited to serotonin reuptake inhibitors, monoamine oxidase inhibitors, tricyclic antidepressants, serotonin agonists, amphetamines, serotonin precursors, serotonin prodrugs, intermediates in the biosynthesis of serotonin, co-factors and pharmaceutically acceptable salts thereof. Such compounds may be given alone or in combination with other serotonin enhancers.

"Serotonergic neurotransmission dysregulation disorder" as used herein refers to any disorder in which an increase or decrease in available serotonin contributes, at least in part, to a disease, disorder, or condition. Examples of such disorders include, but are not limited to, depressive disorder, anxiety disorder, social anxiety disorder, generalized anxiety disorder, bipolar disorder, schizophrenia, autism, epilepsy, mood disorders, alcohol or substance abuse and associated disorders, panic disorder, migraine, obesity, bulimia, anorexia, premenstrual syndrome, menopause, sleep disorders, attention-deficit/hyperactivity disorder (ADHD), Tourette syndrome, aggression, obsessive compulsive disorder, pathological gambling, novelty seeking, borderline personality disorders, antisocial personality disorder, suicidality, eating disorders, sexual dysfunction, dementia, social phobia, fibromyalgia, overactive bladder, chronic fatigue syndrome, chronic pain, sudden infant death syndrome, post-traumatic stress syndrome, and Alzheimer's disease. These terms have their usual meaning in the art (see, e.g., DSM-IV).

"Depression" as used herein has its usual meaning in the art and includes treating subjects with symptoms of depression and treating subjects diagnosed as depressed (e.g., subjects diagnosed as afflicted with unipolar major depression)

"Unipolar major depression" (also called "unipolar depression" or "major depression") as used herein has its usual meaning in the art (see, e.g., DSM-IV), and is typically characterized by the presence of at least five of the following symptoms for at least two weeks: Trouble sleeping or excessive sleeping; a dramatic change in appetite, often with weight gain or loss; fatigue and lack of energy; feelings of worthlessness, self-hate, and inappropriate guilt; extreme difficulty concentrating; agitation, restlessness, and irritability; inactivity and withdrawal from usual activities; feelings of hopelessness and helplessness; recurring thoughts of death or suicide.

"Anxiety" as used herein has its conventional meaning in the art and includes the treatment of subjects exhibiting symptoms of anxiety.

"Substance abuse" as used herein has its usual meaning and includes both alcohol abuse or addiction (e.g., alcoholism, or alcoholic subjects), as well as abuse or addiction to drugs such as narcotics, opiates, stimulants, depressants, etc. (e.g., barbiturates, ecstasy, cocaine, crack cocaine, morphine, heroin, amphetamine, methamphetamine, oxycontin, etc.).

Subjects for screening and/or treatment with the present invention are, in general, human subjects, but may also be other mammalian subjects (e.g., rodent subjects such as mouse or rat, primate subjects such as human or monkey, dog, cat, rabbit, etc.) for veterinary purposes. Subjects includes male and female subjects. The subject may be of any race and any age, including juvenile, adolescent, and adult.

"Treating" as used herein means the medical management of a subject, e.g., a human patient, with the intent to cure, ameliorate, stabilize, or prevent a disease, pathological condition, or disorder. This term includes active treatment, that is, treatment directed specifically toward the improvement or associated with the cure of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. "Treating" also includes symptomatic treatment, that is, treatment directed toward constitutional symptoms of the associated disease, pathological condition, or disorder. Thus "treating" includes submitting or subjecting a subject to a compound which will promote the elimination or reduction of a disease or symptoms of a disease, or which will slow the progression of said disease. For example, a subject may be treated with, synthesized organic molecules, naturally occurring organic molecules, peptides, polypeptides, nucleic acid molecules, and components thereof "Treating" also includes the act of not giving a subject a contra-indicated therapeutic.

"Concurrent administration," "administration in combination," "simultaneous administration" or "administered simultaneously" as used herein, interchangeably mean that the compounds are administered at the same point in time or immediately following one another. In the latter case, the two compounds are administered at times sufficiently close that the results observed are indistinguishable from those achieved when the compounds are administered at the same point in time.

"Enhance the activity of" when used herein to describe the effect of a second active agent on a first active agent means the second active agent is administered in an amount that will (a) increase the treatment efficacy of an otherwise efficacious active agent to an even more efficacious level, as well as (b) increase the treatment efficacy of an otherwise ineffective active agent to an efficacious level.

Tryptophan hydroxylase 2 (Tph2) is known and described at GenBank accession numbers NM_173353 (human); NM_173391 (mouse); and NM_173839 (rat). See also M. Bader and D. Walther, PCT Patent Application WO 2004/007704 (US 20060275759).

1. Tph2 mutation or polymorphism detection/genotyping. In general, the step of detecting the polymorphism of interest, or genotyping a subject, may be carried out by collecting a biological sample containing DNA from the subject, and then determining the presence or absence of the polymorphism of interest in the biological sample. Any biological sample which contains the DNA of that subject may be employed, including tissue samples and blood samples, with blood cells being a particularly convenient source. The nucleotide sequence of the mouse and human Tph2 gene is known and suitable probes, restriction enzyme digestion techniques, or other means of detecting the polymorphism may be implemented based on this known sequence, or the variations described herein, in accordance with standard techniques. See, e.g., U.S. Pat. Nos. 6,027,896 and 5,767,248 to A. Roses et al.

In describing the mutations disclosed herein in the novel proteins described herein, and the nucleotides encoding the same, the naming method is as follows: [amino acid replaced] [amino acid number in sequence of known protein] [alternate amino acid]. For example, for the mouse Tph2 variant disclosed herein, proline at the 447th amino acid in the protein is replaced with arginine (Zhang, X et al., 2004).

The polymorphisms described herein can be detected in accordance with known techniques based upon the known sequence information of the mouse and human Tph2 gene and the information provided herein. Novel nucleic acid sequences and proteins described herein can be isolated from human sources based upon the information provided herein or produced by other means such as site-directed mutagenesis of known or available amino acids, coupled as necessary with techniques for the production of recombinant proteins known in the art.

Determining the presence or absence of DNA containing a polymorphism or mutation of interest may be carried out with an oligonucleotide probe labeled with a suitable detectable group, or by means of an amplification reaction such as a polymerase chain reaction or ligase chain reaction (the product of which amplification reaction may then be detected with a labeled oligonucleotide probe or a number of other techniques). Further, the detecting step may include the step of detecting whether the subject is heterozygous or homozygous for the polymorphism of interest. Numerous different oligonucleotide probe assay formats are known which may be employed to carry out the present invention. See, e.g., U.S. Pat. No. 4,302,204 to Wahl et al.; U.S. Pat. No. 4,358,535 to Falkow et al.; U.S. Pat. No. 4,563,419 to Ranki et al.; and U.S. Pat. No. 4,994,373 to Stavrianopoulos et al. (applicants specifically intend that the disclosures of all U.S. Patent references cited herein be incorporated herein by reference).

Amplification of a selected, or target, nucleic acid sequence may be carried out by any suitable means. See generally D. Kwoh and T. Kwoh, Am. Biotechnol. Lab. 8, 14-25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad. Sci. USA 86, 1173-1177 (1989)), self-sustained sequence replication (or "3SR") (see J. Guatelli et al., Proc. Natl. Acad. Sci. USA 87, 1874-1878 (1990)), the Qβ replicase system (see P. Lizardi et al., Bio-Technology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra).

DNA amplification techniques such as the foregoing can involve the use of a probe, a pair of probes, or two pairs of probes which specifically bind to DNA containing the polymorphism of interest, but do not bind to DNA that does not contain the polymorphism of interest under the same hybridization conditions, and which serve as the primer or primers for the amplification of the DNA or a portion thereof in the amplification reaction. Such probes are sometimes referred to as amplification probes or primers herein.

In general, an oligonucleotide probe which is used to detect DNA containing a polymorphism or mutation of interest is an oligonucleotide probe which binds to DNA encoding that mutation or polymorphism, but does not bind to DNA that does not contain the mutation or polymorphism under the same hybridization conditions. The oligonucleotide probe is labeled with a suitable detectable group, such as those set forth below in connection with antibodies. Such probes are sometimes referred to as detection probes or primers herein.

Probes and primers, including those for either amplification and/or protection, are nucleotides (including naturally occurring nucleotides such as DNA and synthetic and/or modified nucleotides) are any suitable length, but are typically from 5, 6, or 8 nucleotides in length up to 40, 50 or 60 nucleotides in length, or more. Such probes and or primers may be immobilized on or coupled to a solid support such as a bead, chip, pin, or microtiter plate well in accordance with known techniques, and/or coupled to or labeled with a detectable group such as a fluorescent compound, a chemiluminescent compound, a radioactive element, or an enzyme in accordance with known techniques.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. When PCR conditions allow for amplification of all allelic types, the types can be distinguished by hybridization with allelic specific probe, by restriction endonuclease digestion, by electrophoresis on denaturing gradient gels, or other techniques.

Ligase chain reaction (LCR) is also carried out in accordance with known techniques. See, e.g., R. Weiss, Science 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

It will be readily appreciated that the detecting steps described herein may be carried out directly or indirectly. For example, a polymorphism or mutation could be detected by measuring by digestion with restriction enzymes, detection of markers that are linked to the mutation or polymorphism, etc.

Genotype determinations can be compiled to predict either prognosis, drug efficacy, or suitability of a patient for participating in clinical trials of a neurological disease therapeutic. For example, the genotype may be compiled with other patient parameters such as age, sex, disease diagnosis, and known allelic frequency of a representative control population. A determination of the statistical probability of the patient having a particular disease risk, drug response, or patient outcome may be assessed from such genotype determinations. Patient outcome, i.e. a prediction of a patient's likely health status, may include a prediction of the patient's response to therapy, rehabilitation time, recovery time, cure rate, rate of disease progression, predisposition for future disease, or risk of having relapse.

Kits useful for carrying out the methods of the present invention will, in general, comprise one or more oligonucleotide probes and other reagents for carrying out the methods as described above, such as restriction enzymes, optionally packaged with suitable instructions for carrying out the methods.

Particular examples of Tph2 mutations that can be screen for or determined in carrying out the present invention include but are not limited to mutations that encode a change in an amino acid of the encoded protein, said amino acid selected from the group consisting of A65, V66, F68, L77, F84, I94, R97, E105, P152, W153, P155, D162, L175, R191, E211, V223, P244, G251, R276, P277, V278, R285, R294, P308, Y310, E313, A333, I339, A342, S343, L344, A346, K353, V421, E423, A428, A436, R441, Y446, P449, Y450, and Q468. A mutation inducing any change in the normal sequence (the amino acid to the left of the number identifying the amino acid location) is within the scope of the present invention (for example, a change of: I to T; E to G, P to Q; R to Q; G to V; P to L; R to W; Y to D; E to K; L to P; R to Q; Y to C; R to H; P to R; A to V; V to I; L to V; Q to X (where X is a stop codon) etc.).

Particularly preferred are the human P449R mutation, the human R441H mutation the human W153R mutation, the human A65V mutation, the human V66I mutation, the human L175V mutation, and the human Q468X (where X is a stop codon) mutation. Subjects may be determined to be heterozygous or homozygous for the indicated mutation, or may be determined to carry different mutations on the same, or different, alleles.

Note that 43 mutations are identified herein, some identified by sequence analysis and some by sequence identity compared to PAH. Table 1 below lists corresponding mutations in Tph2 in six different species, which corresponding mutations are also useful for carrying out the present invention. It is striking that all 43 amino acids for these mutations are virtually identical in Tph2 in six different species (except in two positions). This strongly indicates that mutations in similar position in Tph2 have a like functional impact on serotonin production in other species.

TABLE 1

Corresponding mutations in additional species.

| human | mouse | rat | chicken | zebrafish | pufferfish |
|---|---|---|---|---|---|
| A65 | A63 | A60 | A64 | A35 | A61 |
| V66 | V64 | V61 | V65 | V36 | V62 |
| F68 | F66 | F63 | F67 | F38 | F64 |
| L77 | L75 | L72 | L76 | L47 | L73 |
| F84 | F82 | F79 | F83 | F54 | F80 |
| I94 | I92 | I89 | I93 | I64 | I90 |
| R97 | R95 | R92 | R96 | R67 | R93 |
| E105 | E103 | E100 | E104 | E75 | E101 |
| P152 | P150 | P147 | P151 | P135 | P148 |
| W153 | W151 | W148 | W152 | W136 | W149 |
| P155 | P153 | P150 | P154 | P138 | P151 |
| D162 | D160 | D157 | D161 | D145 | D158 |
| L175 | L173 | L170 | L174 | L158 | L171 |
| R191 | R189 | R186 | R190 | R174 | R187 |
| E211 | E209 | E206 | E210 | E194 | E207 |
| V223 | V221 | V218 | V222 | V206 | V219 |
| P244 | P242 | P239 | P243 | P227 | P240 |
| G251 | G249 | G246 | G250 | G234 | G247 |
| R276 | R274 | R271 | R275 | R259 | R272 |
| P277 | P275 | P272 | P276 | P260 | P273 |
| V278 | V276 | V273 | V277 | V261 | V274 |
| R285 | R283 | R280 | R284 | R268 | R281 |
| R294 | R292 | R289 | R293 | R277 | R290 |
| P308 | P306 | P303 | P307 | P291 | P304 |
| Y310 | Y308 | Y305 | Y309 | Y293 | Y306 |
| E313 | E311 | E308 | E312 | Y296 | E309 |
| A333 | A331 | A328 | A332 | A316 | A329 |
| I339 | I337 | I334 | I338 | I322 | I335 |
| A342 | A340 | A337 | A341 | A325 | A338 |
| S343 | S341 | S338 | S342 | S326 | S339 |
| L344 | L342 | L339 | L343 | L327 | L340 |
| A346 | A344 | A341 | A345 | A329 | A342 |
| K353 | K351 | K348 | K352 | K336 | K349 |
| V421 | V419 | V416 | V420 | V404 | V417 |
| E423 |  | E418 | E422 | E406 | E419 |
| A428 | A426 | A423 | A427 | A411 | A424 |
| A436 | A434 | A431 | A435 | A419 | A432 |
| R441 | R439 | R436 | R440 | R424 | R437 |
| Y446 | Y444 | Y441 | Y445 | Y429 | Y442 |
| P449 | P447 | P444 | P448 | P432 | P445 |
| Y450 | Y448 | Y445 | Y449 | Y433 | Y446 |
| Q468 | Q466 | Q463 | Q467 |  | Q464 |

In addition to the foregoing, intronic mutations are useful for carrying out the present invention. For example, a G-> A mutation at position 144 in Intron 6 of human TPH2 is useful for carrying out the present invention. This is a non-coding mutation in the Intron 6 and is predicted to cause an alternative splicing variant/mutation of human TPH2. The entire intron 6 in human TPH2 is 6236 base pairs in length; the pertinent portion of exon 6 is shown in panel a of Table 2 below, and the pertinint portion of the mutant intron 6 is shown in panel B of Table 2 below.

TABLE 2

Intron 6 non-coding mutation.

A  GGTCAGCCCATTCCCAGGGTGGAGTATACTGAAGAAGAAACTAAAAC
   TTGGGGTGTTGTATTCCGGGAGCTCTCCAAACTCTATCCCACTCATG
   CTTGCCGAGAGTATTTGAAAAACTTCCCTCTGCTGACTAAATACTGT
   GGCTACAGAGAGGACAATGTGCCTCAACTCGAAGATGTCTCCATGTT
   TCTGAAAG (SEQ ID NO:1)

B  gtaagatttcacacaggctgtctcttattagtcaatatcctcaattg
   ccttccaaggacacaggttgcagcaatggctcttttttccaaaaaagg
   aaaaacagtgatttaaaaaattgttggctttgagccaacaattacct
   gcggccacctgtgggaagcagagcaagggactcagctgcttttgcag
   ctcaggagcttgctgaggcctctttgtggctggttgttgtaaatggt
   aaggcccaaaggatatttgcaagttcagctctgagcttttctgatc
   caggagctgctgtgctgggctacatgagtatgaaatgacctccaaaa
   gtgcctttttatttgctttgttaaaaagtat (SEQ ID NO:2)

The g/a polymorphism is shown in bold underlined font in panel b.

2. Active agents. Active agents used to carry out the present invention are, in general, serotonin enhancers. Numerous serotonin enhancers and serotonin enhancer therapies are known. See, e.g., U.S. Pat. No. 6,218,395.

The serotonin enhancer can be a serotonin reuptake inhibitor or selective serotonin reuptake inhibitor, such as described in U.S. Pat. Nos. 6,552,014; 6,492,366; 6,387,956; 6,369,051; or 5,958,429. Examples of known serotonin reuptake inhibitors that may be used in carrying out the present invention include, but are not limited to:

cianopramine or a pharmaceutically acceptable salt thereof (e.g., 5-[3-(dimethylamino)propyl]-10.11-dihydro-5H-dibenz[b,f]azepine-3-carbonitrile);

citalopram or a pharmaceutically acceptable salt thereof (e.g., 1-[3-(dimethylamino)propyl]-1-(p-fluorophenyl)-1,3-dihydro-isobenzofuran-5-carbonitrile);

escitalopram or a pharmaceutically acceptable salt thereof (e.g., (S)-1-3-dimethylamino-propyl-1-(4'-fluoro-phenyl)-1,3-dihydro-isobenzofuran-5-carbonitril, oxalate);

dapiprazole or a pharmaceutically acceptable salt thereof (e.g., 5,6,7, 8-tetrahydro-3-[2-(4-o-tolyl-1-piperazinyl) ethyl]-1,2,4-triazolo[4,3-a]pyridine (hydrochloride));

desvenlafaxine or a pharmaceutically acceptable salt thereof (e.g., Phenol, 4-[2-(dimethylamino)-1-(1-hydroxycyclohexyl)ethyl]-(Z)-2-butanedioate (1:1) monohydrate);

duloxetine or a pharmaceutically acceptable salt thereof, including LY 223.332, LY264.452 ((−)-enantiomer), LY248.686 (HCl), and Y227.942 (+)-enantiomer) (e.g., (+)—(S)—N-methyl- -(1-naphtyloxy)-2-thiophenepropylamine (HCl));

fluoxetine or a pharmaceutically acceptable salt thereof (e.g., 3-[(p-trifluoromethyl)phenoxy]-N-methyl-3-phenyl-propylamine (hydrochloride));

fluvoxamine or a pharmaceutically acceptable salt thereof (e.g., (E)-5-methoxy-4'-(trifluoromethyl)valerophenone O-(2-amino-ethyl)oxime (hydrogen maleate));

ifoxetine or a pharmaceutically acceptable salt thereof (e.g., (+/−)-cis-4-(2,3-xylyloxy)-3-piperidinol (sulfate));

indalpine or a pharmaceutically acceptable salt thereof (e.g., 3-[2-(4-piperidyl)ethyl]indole);

LY 113.821 or a pharmaceutically acceptable salt thereof (e.g., N-methyl-3-(1-naphthoxy)-3-phenylpropylamine);

mirtazapine or a pharmaceutically acceptable salt thereof (e.g., 1,2,3, 4, 10.14-hexahydro-2 methylpiprazino[2,1-a]pyrido[2,3-c]benzazepine);

nefazodone or a pharmaceutically acceptable salt thereof (e.g., 1-[3-[4-(m-chlorophenyl)-1-piperazinyl]propyl]-3-ethyl-4-(2-phenoxyethyl)-$^2$-1,2,4-triazolin-5-one (HCl));

2-nitroimipramine or a pharmaceutically acceptable salt thereof (e.g., 5-[3-(dimethylamino)propyl]-2-nitro-10.11-dihydro-5H-dibenz[b,f]azepine (hydrochloride);

nortriptyline or a pharmaceutically acceptable salt thereof (e.g., 10.11-dihydro-N-methyl-5H-dibenzo[a,d]cycloheptene-$\Delta^{5,\Gamma}$propylamine (hydrochloride));

paroxetine or a pharmaceutically acceptable salt thereof (e.g., (3S-trans)-3-[(1,3-benzodioxol-5-yloxy)methyl]-4-(4-fluorophenyl)piperidine));

RU 25.591 or a pharmaceutically acceptable salt thereof (e.g., cis-6,7,8,9-tetrahydro-N, N-dimethyl-5-(p-nitrophenoxy)-5H-benzocyclohepten-7-amine (fumarate));

sercloremine or a pharmaceutically acceptable salt thereof (e.g., 4-(5-chloro-2-benzofuranyl)-1-methylpiperidine (hydrochloride));

sertraline or a pharmaceutically acceptable salt thereof (e.g., (+)-cis(1S,4S)-4-(3,4-dichlorophenyl)-1,2,3,4-tetrahydro-N-methyl-1-naphthylamine (HCl));

setiptiline or a pharmaceutically acceptable salt thereof (e.g., 2,3,4,9-tetrahydro-2-methyl-1H-dibenzo[c,f]cyclohepta[1,2-c]pyridine (maleate));

tianeptine or a pharmaceutically acceptable salt thereof (e.g., N-(3-chloro-6,11-dihydro-6-methyldibenzo[c,f][1,2]thiazepin-11-yl)-7-amino-heptanoic acid S, S-dioxide);

trazodone or a pharmaceutically acceptable salt thereof (e.g., 2-[3-[4-(3-chlorophenyl)-1-piperazinyl]propyl]-1,2,4-triazolo[4,3-a]pyridin-3(2H)-one (hydrochloride));

venlafaxine or a pharmaceutically acceptable salt thereof (e.g., (+/−)-1-[2-(dimethylamino)-1-(p-methoxyphenyl)ethyl]cyclohexan-1-ol (HCl))

viqualine or a pharmaceutically acceptable salt thereof (e.g., cis-6-methoxy-4-[3-(3R, 4R)-(3-vinylpiperidyl) propyl]-quinoline); and zimeldine or a pharmaceutically acceptable salt thereof (e.g., (Z)-3-(p-bromophenyl)-N, N-dimethyl-3-(3-pyridyl)allylamine).

The serotonin enhancer can be a monoamine oxidase inhibitor such as described in U.S. Pat. Nos. 6,472,423 and 6,011,054. Examples of monoamine oxidase inhibitors include but are not limited to Isocarboxazid, phenelzine, and tranylcypromine. The serotonin enhancer can be a serotonin agonist such as described in U.S. Pat. Nos. 6,656,172; 6,579,899 and 6,387,907. The serotonin enhancer can be an amphetamine (including derivatives thereof such as phentermine, fenfluramine, and (+)-3,4-methylenedioxyamphetamine. The serotonin enhancer can be a tricyclic antidepressant such as described in U.S. Pat. Nos. 6,368,814; 6,358,944; 6,239,162; and 6,211,171. Examples of tricyclic antidepressants include but are not limited to imipramine, amitriptyline and clomipramine.

The serotonin enhancer can be an anxiolytic such as buspirone or ipsapirone.

The serotonin enhancer can be a precursor or prodrug of serotonin, or an intermediate in serotonin biosynthesis, such as described in U.S. Pat. Nos. 6,579,899; 6,013,622; and 5,595,772. Examples includes tryptophan, 5-hydroxytryptophan, TPH2 co-factor tetrahydrobiopterin and its precursors, a tryptophan-rich diet or dietary supplements of tryptophan.

Decarboxylase inhibitors, particularly peripheral decarboxylase inhibitors, useful for carrying out the present invention include carbidopa (particularly L-carbidopa) and/or benserazide. See, e.g., U.S. Pat. No. 6,387,936.

Tetrahydrobiopterin [(6R)-L-erythro-5,6,7,8-tetrahydrobiopterin (or "BH4"), useful as an active agent in the some embodiments of the present invention, is known. See, e.g., U.S. Pat. Nos. 6,451,788 and 4,920,122. While the present invention is described primarily with reference to BH4, other BH4 enhancers such as folates and analogs thereof, (e.g., methylfolate) as well as estrogen agonists and glucocorticoid antagonists may be used in addition, or in alternative, thereto. Folate analogs are known and described in, for example, U.S. Pat. Nos. 6,808,725; 6,673,381; 6,500,829; and 6,191,133.

3. Pharmaceutical Formulations.

The active compounds described above may be formulated alone or in combination with each other (e.g., in the combinations described above) for administration in a pharmaceutical carrier in accordance with known techniques. See, e.g., Remington, *The Science And Practice of Pharmacy* (9$^{th}$ Ed. 1995).

In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound or compounds. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a active agent, in a unit dosage form, in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

For aerosol delivery to the airway surfaces of a patient the pharmaceutical (e.g., as a dry powder or as liquid particles) the formulation may be prepared in aerosolizable form and provided in an aerosol or inhalation delivery device.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compounds or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

The compositions of this invention can also be administered as a food based preparation, functional food, dietary supplement or nutraceutical. For the purposes of this application, "functional food" is defined as a food engineered or supplemented to give improved nutritional value, "dietary supplement" is defined as a substance produced by isolation, or microbial culture purification that gives health benefits, and "nutraceutical" is defined as a food, or parts of a food, that provide medical or health benefits, including prevention and treatment of clinical conditions and/or symptoms related thereto.

Active agents may be included in a pharmaceutical formulation in an amount ranging from 0.001, 0.01, 0.1 or 1 percent by weight, up to about 10, 20, 50 percent by weight, or more, depending upon the activity of the particular active agent. For example, in some embodiments a pharmaceutical formulation of the invention comprises, consists of, or consists essentially of:

(a) from 0.001, 0.01 or 0.1 to 20 or 40 percent by weight of a serotonin enhancer such as a serotonin reuptake inhibitor;

(b) from 0.1 or 1 to 40 or 60 percent by weight of a serotonin precursor such as 5-hydroxytryptophan;

(c) optionally, 0.001, 0.01 or 0.1 to 20 or 40 percent by weight of a peripheral decarboxylase inhibitor such as carbidopa;

(d) optionally, from 0.1 or 1 to 40 or 60 percent by weight of a BH4 enhancer such as tetrahydrobiopterin; and (e) from 1 to 99.9 percent by weight of a pharmaceutically acceptable carrier.

In some other exemplary embodiments, a pharmaceutical formulation of the invention comprises, consists of, or consists essentially of:
(a) from 0.001, 0.01 or 0.1, up to 20 or 40 percent by weight of a serotonin enhancer such as a serotonin reuptake inhibitor;
(b) from 0.001, 0.01 or 0.1, up to 20 or 40 percent by weight of decarboxylase inhibitor such as carbidopa;
(c) optionally, from 0.1 or 1 to 40 or 60 percent by weight of a BH4 enhancer such as tetrahydrobiopterin;
(d) optionally, from 0.1 or 1 to 40 or 60 percent by weight of a serotonin precursor such as 5-hydroxytryptophan; and
(e) from 1 to 99.9 percent by weight of a pharmaceutically acceptable carrier.

In some other exemplary embodiments a pharmaceutical formulation of the invention comprises, consists of, or consists essentially of
(a) 0.001, 0.01 or 0.1 to 20 or 40 percent by weight of a serotonin enhancer such as a serotonin reuptake inhibitor;
(b) from 0.1 or 1 to 40 or 60 percent by weight of a BH4 enhancer such as tetrahydrobiopterin;
(c) optionally, 0.001, 0.01 or 0.1 to 20 or 40 percent by weight of a peripheral decarboxylase inhibitor such as carbidopa;
(d) optionally, from 0.1 or 1 to 40 or 60 percent by weight of a serotonin precursor such as 5-hydroxytryptophan; and
(e) from 1 to 99.9 percent by weight of a pharmaceutically acceptable carrier.

In other exemplary embodiments, a pharmaceutical formulation of the invention comprises, consists of, or consists consisting essentially of:
(a) from 0.1 or 1 to 40 or 60 percent by weight of a serotonin precursor such as 5-hydroxytryptophan; and
(b) from 0.001, 0.01 or 0.1, up to 20 or 40 percent by weight of decarboxylase inhibitor such as carbidopa;
(c) optionally, from 0.1 or 1 to 40 or 60 percent by weight of a BH4 enhancer such as tetrehydrobiopterin;
(d) from 1 to 99.9 percent by weight of a pharmaceutically acceptable carrier.

And in still other embodiments, a pharmaceutical (this term including neutraceutical) formulation of the invention comprises, consists of, or consists essentially of:
(a) from 0.1 or 1 to 40 or 60 percent by weight of a serotonin precursor such as 5-hydroxytryptophan; and
(b) from 0.1 or 1 to 40 or 60 percent by weight of a BH4 enhancer such as tetrahydrobiopterin; and
(c) from 1 to 99.9 percent by weight of a pharmaceutically acceptable carrier (in the case of a neutraceutical optionally from 1 to 99.9 percent by weight of other food ingredients such as fats, proteins, carbohydrates, and combinations thereof).

Such formulations may be provided in any suitable form including those described above, such as tablets, capsules, suppositories, inhalation or aerosolizable formulations, formulations in an inhalation delivery device, parenterally injectable formulations. etc. In the case of a neutraceutical composition, the formulation may be provided in the form of a bar, beverage, drink, snack food, etc.

4. Subjects, Dosage and Routes of Administration.

Subjects to be treated by the methods of the invention are, in some embodiments (such as those involving administration of a serotonin enhancer such as a serotonin reuptake inhibitor in combination with a serotonin precursor and/or a peripheral decarboxylase inhibitor) those exhibiting symptoms of a serotonin neurotransmission dysregulation disorder (particularly depression, anxiety, or substance abuse, although it will be understood that subjects afflicted with other serotonin neurotransmission dysregulation disorders such as set forth above may be treated as well). Subjects may be those previously determined to be non-responsive or insufficiently responsive to treatment therapy with a serotonin enhancer such as a serotonin reuptake inhibitor alone (e.g., subjects who exhibited no benefit or improvement in symptoms to administration of a serotonin enhancer such as a serotonin reuptake inhibitor, or subjects who exhibited insufficient benefit or improvement in symptoms to administration of a serotonin enhancer such as a serotonin reuptake inhibitor).

Subjects may, in some preferred embodiments, be genotyped or determined to carry a Tph2 mutation prior to initiation of the treatments described herein. Such subjects may be more confidently administered the treatments described herein based on a greater expectation of likely clinical benefit of these treatments, based on the greater understanding of the underlying genetic and physiological basis of the disorder as described herein.

The active compounds may be administered to the subject by any suitable route, including those indicated with respect to particular formulations above. Thus suitable routes of administration include oral administration, buccal administration, parenteral injection, inhalation or aerosol administration, transcutaneous administration, etc.

The therapeutically effective dosage of any specific active compound, the use of which is in the scope of present invention, will vary somewhat from compound to compound, and patient to patient, and will depend upon the condition of the patient and the route of delivery.

For example, a serotonin enhancer such as a serotonin reuptake inhibitor can be administered to the average adult human for the treatment of the disorders described herein in an amount of from about 0.1 mg to about 2000 mg, preferably from about 1 mg to about 200 mg per unit dose.

A peripheral decarboxylase inhibitor such as carbidopa or benserazide can, in some embodiments, be administered to an average adult human subject in an amount of from 5 or 10 to 25, 50 or 100 milligrams per unit dose.

A precursor or prodrug of serotonin, or an intermediate in serotonin biosynthesis, such as 5-hydroxytryptophan, may be administered in an amount of from about 1, 2 5 or 10 milligrams up to 0.1, 0.5, 1 or 4 grams per unit dose.

Administration of unit doses of active agents, alone or in combination, may be one or several times daily, for example 2, 3, 4 or 8 times, giving for example, 1, 2 or 3 doses each time.

The present invention is explained in greater detail in the following non-limiting Examples.

EXAMPLES

TPH1 and 2 convert tryptophan to 5-hydroxytryptophan, which is then decarboxylated by aromatic amino acid decarboxylase (AADC) to serotonin. The two enzymes belong to the family of aromatic amino acid hydroxylases. Members of this family include phenylalanine hydroxylase (PAH) and tyrosine hydroxylase (TH) respectively involved in the synthesis of tyrosine and L-Dopa, the precursor of dopamine. Both TH and TPH catalyze the rate limiting steps in the synthesis of dopamine and serotonin. There is a high degree of sequence conservation in the genes for these four different enzymes. These enzymes show considerable structural similarities and require the same co-factor for function (Fitzpatrick, 1999). Over 400 mutations have been previously identified in the PAH gene and these mutations, which result in reduced enzyme activity, produce hyperphenylalaninemia causing of one of the most prevalent condition identified in newborns, phenylketonuria (PKU) (Scriver et al, 2003).

Figure 1:
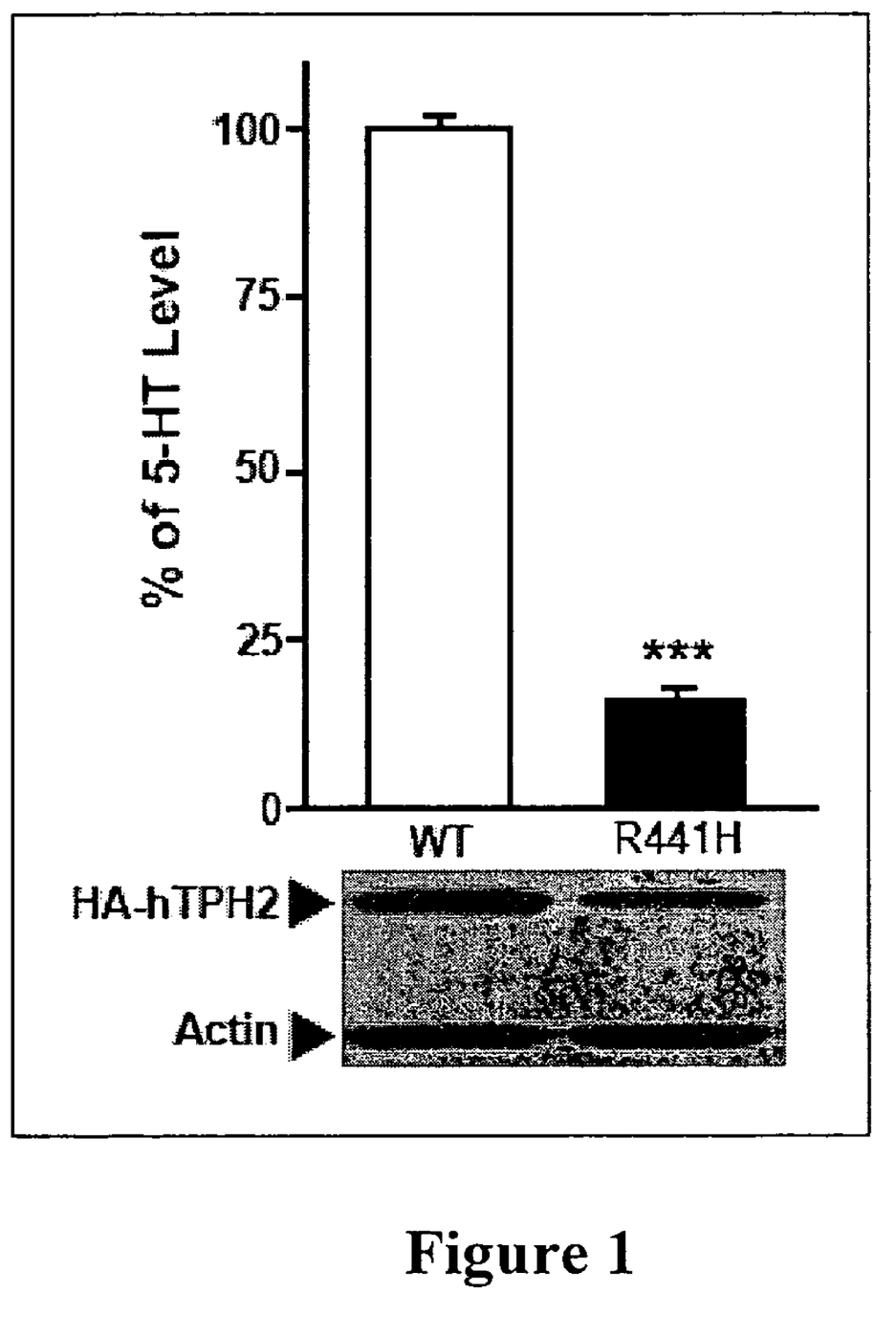
FIG. 1. Serotonin levels in PC12 cells expressing R441H hTPH2 were lower than those in PC12 cells expressing WT hTPH2 (n=8 experiments).

A (G1463A) SNP which replaces a highly conserved Arg441 (CGT) with His441 (CAT) has been identified resulting in ~80% decrease in serotonin levels as compared to wild type TPH2 when expressed in PC12 cells (FIG. 1), indicating a severe loss-of-function phenotype of TPH2 (R441H) in serotonin synthesis. In addition, allele-specific genotyping has identified that 9 subjects were found to carry the 1463A allele in a cohort of 87 subjects diagnosed with unipolar major depression, while only 3 subjects from a cohort of non-unipolar major depression (or control) subjects (N=279) were found to carry the 1463A allele (Table 3). The presence of this functional SNP in unipolar major depression subjects versus non-unipolar major depression subjects was statistically significant (P=1.989E-04 by Fisher's Exact Test). Moreover, among these 9 unipolar major depression subjects, 7 had family history of mental illness or drug and alcohol abuse, 6 had suicidal ideation or attempt and 4 had generalized anxiety symptoms. Interestingly, 7 subjects exhibited lack of responsiveness to SSRI, while 2 subjects were responsive only to high doses of SSRI (Table 3). However, among the 3 non-unipolar major depression (or control) subjects carrying 1463A allele, one subject had generalized anxiety symptoms, while the other two had mild depression and family history of mental illness or drug and alcohol abuse (Table 3), indicating a higher susceptibility for certain neuropsychiatric disorders in the presence of 1463A allele. Therefore, identification of a loss-of-function mutation in hTPH2 provides direct evidence for a role of brain serotonin synthesis in unipolar major depression.

Flattem, N. L. and Blakely, R. D., Modified structure of the human serotonin transporter promoter. *Mol Psychiatry* 5, 110-115 (2000).

Frazer, A., Pharmacology of antidepressants. *J. Clin. Psychopharmacol.* 17 Suppl 1, 2S-18S (1997).

Geyer, M. A., Serotonergic functions in arousal and motor activity. *Behav. Brain Res.* 73, 31-35 (1996).

Scriver, C. R., Hurtubise, M., Konecki, D., Phommarinh, M., Prevost, L., Erlandsen, H., Stevens, R., Waters, P. J., Ryan, S., McDonald, D. and Sarkissian, C., PAHdb 2003: What a locus-specific knowledgebase can do. *Hum. Mutat.* 21, 333-344 (2003).

Snyder, S. H. and Peroutka, S. J., A possible role of serotonin receptors in antidepressant drug action. *Pharmacopsychiatria* 15, 131-134 (1982).

Tamminga, C. A., Serotonin and schizophrenia. *Biol. Psychiatry* 44, 1079-1080 (1998).

Tecott, L. H., The genes and brains of mice and men. *Am. J. Psychiatry* 160, 646-656 (2003).

Veenstra-VanderWeele, J., Anderson, G. M. and E. H. Cook Jr., E. H., Pharmacogenetics and the serotonin system: initial studies and future directions. *Eur. J. Pharmacol.* 410, 165-181 (2000).

TABLE 3

Summary of genotype and history of subjects.

| Patient I.D. | Sex | Age | Allele | Family History | Suicidality | Anxiety | SSRI Response | Note |
|---|---|---|---|---|---|---|---|---|
| Unipolar Major Depression Patients | | | | | | | | |
| N = 87 | | | | | | | | |
| 1202 | F | 72 | A/A | − | + | − | + | Sertraline 200 mg |
| 1294 | M | 80 | G/A | + | + | − | − | |
| 1496 | M | 74 | A/A | − | − | + | + | Sertraline 100 mg |
| 1745 | M | 71 | G/A | + | − | + | − | |
| 1747 | M | 82 | G/A | + | + | − | − | |
| 1839 | F | 69 | G/A | + | − | − | − | |
| 1851 | F | 65 | G/A | + | + | − | − | |
| 1902 | F | 77 | A/A | + | + | + | − | |
| 1975 | M | 64 | G/A | + | + | + | − | |
| Non-Unipolar Major Depression Subjects | | | | | | | | |
| N = 279 | | | | | | | | |
| 1174 | | | A/A | − | | + | | |
| 1541 | | | G/A | + | | − | | Mild depression |
| 1996 | | | G/A | + | | − | | Mild depression |

Family history: family history for mental illness, drug or alcohol abuse
Suicidality: suicidal ideation or attempt
Anxiety: three or more anxiety symptoms

REFERENCES

Aghajanian, G. K. and Marek, G. J., Serotonin model of schizophrenia: emerging role of glutamate mechanisms. *Brain Res. Brain Res. Rev.* 31, 302-312 (2000).

Blier, P. and Abbott, F. V., Putative mechanisms of action of antidepressant drugs in affective and anxiety disorders and pain. *J. Psychiatry Neurosci.* 26, 37-43 (2001).

Fitzpatrick, P. F., Tetrahydropterin-dependent amino acid hydroxylases. *Annu. Rev. Biochem.* 68, 355-381 (1999).

Walther, D. J., Peter, J. U., Bashammakh, S., Hortnagl, H., Voits, M., Fink, H. and Bader, M., Synthesis of serotonin by a second tryptophan hydroxylase isoform. *Science* 299, 76 (2003).

Zhang, X., Beaulieu, J-. M., Sotnikova, T. D., Gainetdinov, R. R. and Caron, M. G., Tryptophan hydroxylase-2 controls brain serotonin synthesis. *Science* 305, 217 (2004).

The foregoing is illustrative of the present invention, and is not to be construed as limiting thereof. The invention is defined by the following claims, with equivalents of the claims to be included therein.

That which is claimed is:

1. A method of treating a human subject for unipolar major depression, comprising:
   determining the presence or absence of a human R441H tryptophan hydroxylase 2 (Tph2) mutation in said subject; and then, if said subject possesses said human R441H Tph2 mutation;
   administering said subject a serotonin reuptake inhibitor in an amount effective to treat said disorder; and
   concurrently administering said subject 5-hydroxytryptophan in an amount effective to enhance the activity of said serotonin reuptake inhibitor.

2. The method of claim 1, wherein said serotonin reuptake inhibitor is selected from the group consisting of citalopram, fluvoxamine, fluoxetine, sertraline, paroxetine, escitalopram, duloxetine, venlafaxine, and pharmaceutically acceptable salts thereof.

3. The method of claim 1, further comprising the step of concurrently administering said subject a peripheral decarboxylase inhibitor in an amount effective to reduce peripheral degradation of said 5-hydroxytryptophan.

4. The method of claim 3, wherein said peripheral decarboxylase inhibitor is selected from the group consisting of carbidopa and benserazide.

5. The method of claim 1, further comprising the step of concurrently administering said subject tetrahydrobiopterin.

* * * * *

UNITED STATES PATENT AND TRADEMARK OFFICE
CERTIFICATE OF CORRECTION

PATENT NO. : 7,517,908 B2
APPLICATION NO. : 11/133867
DATED : April 14, 2009
INVENTOR(S) : Ranga R. Krishnan et al.

It is certified that error appears in the above-identified patent and that said Letters Patent is hereby corrected as shown below:

Please correct "Gainetdinova" to read --Gainetdinov--

Signed and Sealed this

Eighteenth Day of August, 2009

David J. Kappos
*Director of the United States Patent and Trademark Office*

UNITED STATES PATENT AND TRADEMARK OFFICE
CERTIFICATE OF CORRECTION

PATENT NO. : 7,517,908 B2
APPLICATION NO. : 11/133867
DATED : April 14, 2009
INVENTOR(S) : Ranga R. Krishnan et al.

It is certified that error appears in the above-identified patent and that said Letters Patent is hereby corrected as shown below:

Title Page, Item (75) Inventors,
Please correct "Gainetdinova" to read --Gainetdinov--

This certificate supersedes the Certificate of Correction issued August 18, 2009.

Signed and Sealed this

Eighth Day of September, 2009

David J. Kappos
*Director of the United States Patent and Trademark Office*

```
                              SEQUENCE LISTING

<160> NUMBER OF SEQ ID NOS: 2

<210> SEQ ID NO 1
<211> LENGTH: 196
<212> TYPE: DNA
<213> ORGANISM: Homo sapiens

<400> SEQUENCE: 1
ggtcagccca ttcccagggt ggagtatact gaagaagaaa ctaaaacttg gggtgttgta        60
ttccgggagc tctccaaact ctatcccact catgcttgcc gagagtattt gaaaaacttc       120
cctctgctga ctaaatactg tggctacaga gaggacaatg tgcctcaact cgaagatgtc       180
tccatgtttc tgaaag                                                       196

<210> SEQ ID NO 2
<211> LENGTH: 360
<212> TYPE: DNA
<213> ORGANISM: Homo sapiens

<400> SEQUENCE: 2
gtaagatttc acacaggctg tctcttatta gtcaatatcc tcaattgcct tccaaggaca        60
caggttgcag caatggctct tttcccaaaa aaggaaaaac agtgatttaa aaaattgttg       120
gctttgagcc aacaattacc tgcggccacc tgtgggaagc agagcaaggg actcagctgc       180
ttttgcagct caggagcttg ctgaggcctc tttgtggctg gttgttgtaa atggtaaggc       240
ccaaaggata tttgcaagtt cagctctgag ctttttctga tccaggagct gctgtgctgg       300
gctacatgag tatgaaatga cctccaaaag tgcctttta tttgctttgt taaaaagtat       360
```